(12) United States Patent
Luyken et al.

(10) Patent No.: US 8,530,690 B2
(45) Date of Patent: Sep. 10, 2013

(54) PROCESS FOR ISOMERIZING CIS-2-PENTENENITRILE TO 3-PENTENENITRILES

(75) Inventors: Hermann Luyken, Ludwigshafen (DE); Peter Pfab, Shaker Heights, OH (US); Robert Baumann, Mannheim (DE); Andreas Leitner, Linz (AT); Tobias Aechtner, Mannheim (DE)

(73) Assignee: BASF SE (DE)

( * ) Notice: Subject to any disclaimer, the term of this patent is extended or adjusted under 35 U.S.C. 154(b) by 233 days.

(21) Appl. No.: 13/081,664

(22) Filed: Apr. 7, 2011

(65) Prior Publication Data

US 2011/0288326 A1    Nov. 24, 2011

Related U.S. Application Data

(60) Provisional application No. 61/321,519, filed on Apr. 7, 2010.

(51) Int. Cl.
*C07C 255/07*    (2006.01)

(52) U.S. Cl.
USPC .......................................................... 558/462

(58) Field of Classification Search
USPC .............. 439/65, 66, 70, 71, 81, 91; 558/462
See application file for complete search history.

(56) References Cited

U.S. PATENT DOCUMENTS

| | | | |
|---|---|---|---|
| 5,070,202 A | 12/1991 | Herkes | |
| 6,384,263 B1 * | 5/2002 | Herkes | .......................... 558/451 |
| 7,566,800 B2 | 7/2009 | Scheidel et al. | |
| 7,612,224 B2 | 11/2009 | Scheidel et al. | |
| 7,816,551 B2 | 10/2010 | Jungkamp et al. | |

FOREIGN PATENT DOCUMENTS

| | | |
|---|---|---|
| WO | WO-2005/73172 A1 | 8/2005 |
| WO | WO-2005/73176 A1 | 8/2005 |
| WO | WO-2005/73177 A1 | 8/2005 |

* cited by examiner

*Primary Examiner* — Nyeemah A Grazier

(57) ABSTRACT

A process for isomerizing cis-2-pentenenitrile to 3-pentenenitriles, by isomerizing cis-2-pentenenitrile with amidines, tertiary amines or mixtures thereof as a catalyst at temperatures of 80 to 200° C. and a pressure of 0.01 to 50 bar.

6 Claims, No Drawings

PROCESS FOR ISOMERIZING CIS-2-PENTENENITRILE TO 3-PENTENENITRILES

CROSS-REFERENCE TO RELATED APPLICATIONS

This application claims benefit (under 35 USC 119(e)) of U.S. Provisional application 61/321,519, filed Apr. 7, 2010 which is incorporated by reference.

BACKGROUND OF THE INVENTION

The present invention relates to an improved process for isomerizing cis-2-pentenenitrile to 3-pentenenitriles in the presence of tertiary amines or of amidines as catalysts.

WO-A-05/73176 discloses isomerizing cis-2-pentenenitrile to 3-pentenenitriles with the aid of homogeneously dissolved amines as catalysts, selected from the group of $C_1$- to $C_{20}$-mono- and diamines.

U.S. Pat. No. 5,070,202 discloses that cis-2-pentenenitrile forms Michael adducts with primary and secondary amines at temperatures of 20 to 200° C.

A disadvantage of these isomerizations is that Michael adducts form from cis-2-pentenenitrile and the amines mentioned as catalysts.

BRIEF SUMMARY OF THE INVENTION

It was therefore an object of the present invention to remedy the aforementioned disadvantages.

Accordingly, a novel and improved process for isomerizing cis-2-pentenenitrile to 3-pentenenitriles has been found, which comprises isomerizing cis-2-pentenenitrile with amidines, tertiary amines or mixtures thereof as a catalyst at temperatures of 80 to 200° C. and a pressure of 0.01 to 50 bar.

DETAILED DESCRIPTION OF THE INVENTION

The process according to the invention can be performed as follows:

cis-2-Pentenenitrile can be converted batchwise or preferably continuously with a catalyst at temperatures of 80 to 200° C., preferably 90 to 150° C., more preferably 100 to 150° C., and a pressure of 0.01 to 50 bar, preferably 0.1 to 30 bar, more preferably 0.5 to 20 bar, especially standard pressure (atmospheric pressure).

The tertiary amines, preferably the tertiary alkyl-, cycloalkyl-, alkylcycloalkylamines and mixtures thereof, should have a boiling point equal to or lower than, i.e. 0 to 50° C., preferably 1 to 40° C., more preferably 3 to 30° C., especially 4 to 20° C. and most preferably 5 to 10° C. lower than, that of cis-2-pentenenitrile (boiling point 127° C./1013 mbar), or higher than, i.e. 1 to 50° C., preferably 2 to 30° C., more preferably 3 to 20° C. and especially 5 to 10° C. higher than, that of cis-3-pentenenitrile (boiling point 146° C./1013 mbar).

The mixtures of tertiary amines and amidines should have a boiling point equal to or lower than, i.e. 0 to 50° C., preferably 1 to 40° C., more preferably 3 to 30° C., especially 4 to 20° C. and most preferably 5 to 10° C. lower than, that of cis-2-pentenenitrile, or higher than, i.e. 1 to 50° C., preferably 2 to 30° C., more preferably 3 to 20° C. and especially 5 to 10° C. higher than, that of cis-3-pentenenitrile.

The aminopyridines, the imidazoles, the bicyclic amidines II or mixtures thereof should have boiling points higher than, i.e. 1 to 50° C., preferably 2 to 30° C., more preferably 3 to 20° C. and especially 5 to 10° C. higher than, that of cis-3-pentenenitrile.

The isomerization can be performed in any suitable apparatus, such as tubular reactors or stirred autoclaves, for example in a stirred autoclave under ambient pressure, i.e. at standard pressure (atmospheric pressure), or under the pressure which is established at the particular reaction temperature.

The molar ratio of catalyst to cis-2-pentenenitrile can be varied within wide limits and is generally 0.1:1 to 1:1 mol, preferably 0.1:1 to 0.5:1, more preferably 0.15:1 to 0.3:1 mol.

The reaction output of the isomerization can be worked up by distillation. Unconverted cis-2-pentenenitrile as the top product, optionally together with catalysts having a lower boiling point than cis-2-pentenenitrile, can be reused in a further isomerization batch. trans-3- and trans-2-Pentenenitrile, optionally after removal and recycling of catalysts having a higher boiling point than cis-3-pentenenitrile, can be used for pentenenitrile hydrocyanation.

Suitable cis-2-pentenenitrile is pure cis-2-pentenenitrile, mixtures which comprise cis-2-pentenenitrile, or by-product streams from the hydrocyanation of 1,3-butadiene which comprise cis-2-pentenenitrile, preferably more than 50% by weight of cis-2-pentenenitrile, more preferably more than 50% by weight of cis-2-pentenenitrile.

Suitable catalysts for the isomerization are nitrogen bases such as tertiary amines or mixtures thereof, or amidines or mixtures thereof, or mixtures of tertiary amines and amidines. The catalysts are also referred to hereinafter as nitrogen bases.

Suitable tertiary amines are tertiary alkyl-, cycloalkyl- or alkylcycloalkylamines, aminopyridines, imidazoles, or mixtures thereof, preferably tertiary alkyl- or cycloalkylamines, imidazoles, or mixtures thereof, more preferably tertiary alkylamines.

Suitable amidines are bicyclic amidines II.

Suitable tertiary amines are amines of the general formula I $[R^1R^2R^3N]$ in which the $R^1$, $R^2$, $R^3$ radicals are each independently $C_1$- to $C_{20}$-alkyl, preferably $C_1$- to $C_8$-alkyl, more preferably $C_1$- to $C_6$-alkyl such as methyl, ethyl, n-propyl, isopropyl, n-butyl, isobutyl, sec-butyl, tert-butyl, n-pentyl, isopentyl, n-hexyl, isohexyl, $C_3$- to $C_{12}$-cycloalkyl, preferably $C_4$- to $C_8$-cycloalkyl, more preferably $C_5$- to $C_7$-cycloalkyl such as cyclopentyl, cyclohexyl and cycloheptyl, $C_3$- to $C_{12}$-cycloalkyl mono- to trisubstituted by $C_1$- to $C_4$-alkyl such as methyl, ethyl, n-propyl, isopropyl, n-butyl, isobutyl, sec-butyl or tert-butyl, preferably $C_4$- to $C_8$-cycloalkyl, more preferably $C_5$- to $C_7$-cycloalkyl such as cyclopentyl, cyclohexyl, cycloheptyl, or mixtures thereof, or two of the $R^1$, $R^2$, $R^3$ radicals together are a linear $C_4$- to $C_9$ chain, preferably $C_5$- to $C_7$ chain, which is optionally substituted by $C_1$- to $C_4$-alkyl such as methyl, ethyl, n-propyl, isopropyl, n-butyl, isobutyl, sec-butyl or tert-butyl, and may additionally comprise a nitrogen, oxygen or sulfur atom. The $R^1$, $R^2$, $R^3$ radicals may also be joined so as to form a tertiary amine which independently comprises two five- to seven-membered rings.

Examples of suitable tertiary amines of the formula I are trimethylamine, triethylamine, methyldiethylamine, dimethylethylamine, tributylamine, ethyldipropylamine, tripropylamine, trihexylamine, tricyclohexylamine, ethyldicyclohexylamine, N-methylpiperidine, N-ethylpiperidine, N-methylpyrrolidine, N-ethylpyrrolidine, N-propylazepine, N-ethylmorpholine, N,N'-dimethylpiperazine or mixtures of these tertiary amines, preferably triethylamine.

Suitable tertiary amines of the formula I which independently comprise two five- to seven-membered rings are, for example, tropane, granatane and quinuclidine.

Further tertiary amines are 4-aminopyridines where the two hydrogen atoms of the amino group may be as defined for the $R^1$, $R^2$, $R^3$ radicals.

Suitable 4-aminopyridines are, for example, N,N-dimethyl-4-aminopyridine, N,N-diethyl-4-aminopyridine, 4-morpholinopyridine or 4-piperazinopyridine, preferably N,N-dimethyl-4-aminopyridine or N,N-diethyl-4-aminopyridine, more preferably N,N-dimethyl-4-aminopyridine.

Suitable tertiary amines are additionally N-substituted imidazoles, where the substituent is $C_1$- to $C_{20}$-alkyl, preferably $C_1$- to $C_8$-alkyl such as methyl, ethyl, n-propyl, isopropyl, n-butyl, isobutyl, sec-butyl, tert-butyl, n-pentyl, isopentyl, n-hexyl, isohexyl, more preferably $C_1$- to $C_4$-alkyl such as methyl, ethyl, n-propyl, isopropyl, n-butyl, isobutyl, sec-butyl or tert-butyl, especially $C_1$- to $C_2$-alkyl such as methyl or ethyl.

Suitable imidazoles are, for example, N-methyl-, N-ethyl- or N-propylimidazole.

Suitable amidines are, for example, bicyclic amidines of the formula II

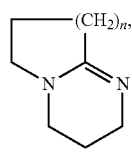

in which n is 1, 2 or 3, preferably 1 or 3, more preferably 1. Examples thereof are 1,5-diazabicyclo[4.3.0]-5-nonene (DBN) and 1,8-diazabicyclo[5.4.0]-7-undecene (DBU).

cis-2-Pentenenitrile, the starting material for the isomerization to 3-pentenenitriles, forms, for example, in the hydrocyanation of 3-pentenenitriles to adiponitrile.

The two-stage preparation of adiponitrile proceeding from butadiene and hydrogen cyanide is known (Hans-Jürgen Arpe, Industrielle Organische Chemie [Industrial Organic Chemistry], 6th edition 2007, Wiley-VCH publishers, pages 272 to 273):

In the first reaction step, butadiene is hydrocyanated in liquid phase in the presence of nickel(0)-tritolyl phosphite complexes as catalysts. A mixture of isomeric pentenenitriles and methylbutenenitriles is isolated, especially 3-pentenenitriles and 2-methyl-3-butenenitriles. The 2-methyl-3-butenenitriles are isomerized to 3-pentenenitriles.

In the second reaction step, 3-pentenenitrile is hydrocyanated with hydrogen cyanide in liquid phase. The step is conducted in the presence of the same nickel(0)-tritolyl phosphite complexes, to which a Lewis acid, for example zinc chloride, is added.

Adiponitrile, further dinitriles and the nickel(0) catalyst complex are removed from the hydrocyanation output. Optionally after regeneration, the catalyst is recycled into the hydrocyanation.

The organic phase obtained in the workup comprises essentially unsaturated $C_5$-mononitriles selected from the group of cis-2-pentenenitrile, trans-3-pentenenitrile, cis-3-pentenenitrile, 4-pentenenitrile, trans-2-pentenenitrile, cis-2-methyl-2-butenenitrile, trans-2-methyl-2-butenenitrile, 2-methyl-3-butenenitrile.

This $C_5$-mononitrile stream may comprise 0.1 to 10% by weight of cis-2-pentenenitrile, especially 1 to 5% by weight of cis-2-pentenenitrile.

For batchwise isomerization, a cis-2-pentenenitrile obtained in this way can first be removed by distillation from the $C_5$-mononitrile mixture. For the isomerization, a cis-2-pentenenitrile with a purity of >50%, preferably >70%, can be used.

In a particularly preferred embodiment, the isomerization can be performed continuously in integrated mode with nitrogen bases having equal or lower boiling points compared to cis-2-pentenenitrile as catalysts. Integrated mode is understood to mean that cis-2-pentenenitrile, mixtures of 3-pentenenitrile and trans-2-pentenenitrile and the nitrogen base are recycled continuously into the particular process stages, which means that all recycle streams are self-contained.

This object is achieved by a continuous integrated process for isomerizing cis-2-pentenenitrile to 3-pentenenitriles, by
a) hydrocyanating 3-pentenenitriles or a mixture comprising 3-pentenenitriles to adiponitrile in the presence of nickel (0)-phosphorus ligand complexes as catalysts,
b) removing adiponitrile, 2-methylglutaronitrile and nickel (0)-phosphorus ligand complex from the hydrocyanation output,
c) isomerizing the cis-2-pentenenitrile in the organic phase thus obtained, comprising essentially unsaturated C5-mononitriles such as cis- and trans-3-pentenenitrile, 4-pentenenitrile, trans-2-pentenenitrile, cis-2-methyl-2-butenenitrile, trans-2-methyl-2-butenenitrile, 2-methyl-3-butenenitrile, to 3-pentenenitriles with the aid of a nitrogen base of the formula I as a catalyst, the boiling point of which is equal to or lower than that of cis-2-pentenenitrile at standard pressure,
d) feeding the organic phase which comprises essentially unsaturated C5-mononitriles and is obtained in c) to a distillation column K1, removing cis-2-pentenenitrile and cis- and trans-2-methyl-2-butenenitrile via the top of the distillation column K1, and 3-pentenenitrile and trans-2-pentenenitrile via the bottom, and recycling the latter into the reaction step for hydrocyanation of 3-pentenenitriles,
e) feeding the top product of column K1 to a distillation column K2, and removing and discharging trans-2-methyl-2-butenenitrile as the bottom product of column K2,
f) feeding the top product of column K2 and a nitrogen base having a boiling point equal to or lower than that of cis-2-pentenenitrile to a reactor R1, and feeding the reaction product of the reactor R1 and the tertiary amine having a boiling point equal to or lower than that of cis-2-pentenenitrile to a distillation column K3,
g) recycling the top product of the distillation column K3, which consists predominantly of the tertiary amine, into the reactor R1 and discharging a substream of the top product comprising cis-2-methyl-2-butenenitrile, tertiary amine and cis-2-pentenenitrile, recycling a mixture of cis-2-pentenenitrile, trans-3-pentenenitrile, trans-2-pentenenitrile and tertiary base from a side draw into distillation column K1, and discharging high boilers as the bottom product.

The continuous isomerization of cis-2-pentenenitrile to 3-pentenenitriles using tertiary amines I having lower boiling points than cis-2-pentenenitrile can be performed in apparatus known to those skilled in the art. Suitable apparatus for the distillation is as described, for example, in: Kirk-Othmer, Encyclopedia of Chemical Technology, 4th ed., vol. 8, John Wiley & Sons, New York, 1996, pages 334 to 338, such as sieve tray columns, bubble-cap tray columns, columns with structured packing, columns with random packing, which may also be operated as dividing wall columns. This distillation apparatus is in each case equipped with suitable apparatus for evaporation, such as falling-film evaporators, thin-film evaporators, multiphase helical tubular evaporators, natural circulation evaporators, or forced circulation flash evaporators, and with apparatus for condensation of the vapor stream. Distillation can be performed in a plurality of, such as two or three, apparatuses. The distillation can additionally be effected in one stage in the manner of a partial evaporation of the feed stream.

Steps a) to c) have already been described on pages 3 and 4.

Step d):

In step d), the organic phase which comprises essentially $C_5$-mononitriles and is obtained in step c) is fed to a distillation column K1 which possesses 20 to 40 theoretical plates and is operated at a bottom temperature in the range from 70 to 145° C. and a pressure of 100 to 1000 mbar.

cis-2-Pentenenitrile, cis- and trans-2-methyl-2-butenenitrile and recycled tertiary amine I are distilled via the top of the column K1. The bottom products drawn off are 3-pentenenitriles and trans-2-pentenenitrile, which are recycled into step a).

It may be advantageous to draw off 3-pentenenitriles and trans-2-pentenenitrile from a side draw, recycle them into step a) and optionally discharge high boilers as bottom products.

Step e):

The top product of column K1 is fed to a column K2 which has 20 to 40 theoretical plates and is operated at a bottom temperature in the range from 60 to 140° C. and a pressure of 50 to 100 mbar.

The top product of column K2 comprises cis-2-pentenenitrile, cis-2-methyl-2-butenenitrile and recycled tertiary amine I. The bottom product discharged is trans-2-methyl-2-butenenitrile.

Step f):

The top product of column K2 is fed to a reactor R1 in which the predominant portion of the isomerization is effected. Additionally fed to the column K2 is a sufficient amount of tertiary amine I that amine losses in the cycle which result from discharging are compensated for.

The inventive isomerization can be performed in any suitable apparatus known to those skilled in the art. Useful apparatus for the reaction is thus customary apparatus as described, for example, in: Kirk-Othmer, Encyclopedia of Chemical Technology, 4th ed., vol. 20, John Wiley & Sons, New York, 1996, pages 1040 to 1055, such as stirred tank reactors, loop reactors, gas circulation reactors, bubble column reactors or tubular reactors, preferably tubular reactors, in each case optionally with apparatus for heat transfer. The reaction can be performed in a plurality of, such as two or three, apparatuses.

Particular preference is given to a stirred tank cascade with 2 to 4, especially 3, stirred tanks, or a flow tube.

The isomerization reactor is operated at temperatures of 100 to 150° C., preferably 100 to 130° C., and pressures of 1 to 20 bar. The residence times in the reactor are 0.5 to 5 hours, preferably 1 to 3 hours. The cis-2-pentenenitrile conversion is 5 to 30%, preferably 10 to 25% and more preferably 10 to 20%.

Step g):

The reaction discharge of reactor R1, which comprises 3-pentenenitriles as isomerization products, trans-2-pentenenitrile, cis-2-methyl-2-butenenitrile, unconverted cis-2-pentenenitrile and tertiary amine I, is fed to a column K3.

Column K3 has 10 to 20 theoretical plates and is operated at a bottom temperature in the range from 100 to 150° C. and a pressure of 100 to 1000 mbar.

The top product of column K3, which consists predominantly of the tertiary amine I, is recycled into reactor R1. A substream of the top product is discharged in order to prevent accumulation of cis-2-methyl-2-butenenitrile. A stream comprising trans-3-pentenenitrile and trans-2-methyl-2-butenenitrile in addition to predominantly cis-2-pentenenitrile and tertiary amine I is withdrawn from a side draw. This stream is recycled to column K1. High boilers are discharged as the bottom product.

It is also possible to use nitrogen bases which have boiling points higher, especially 5 to 10° C. higher, than cis-3-pentenenitrile at standard pressure as catalysts in step f) for the isomerization of cis-2-pentenenitrile to 3-pentenenitriles. They can, for example, be withdrawn together with high boilers as the bottom product of column K3 and, optionally after removal of the high boilers, for example in a column or a thin-film evaporator, recycled into reactor R1.

In a preferred embodiment of the invention, which is employable for nitrogen bases which have boiling points lower than cis-2-pentenenitrile at standard pressure, or higher, especially at least 5 to 10° C. higher, than cis-3-pentenenitrile at standard pressure, the reactor R1 is replaced by a reaction column. WO-A-05/73177 describes reaction columns for the isomerization of cis-2-pentenenitrile to 3-pentenenitriles in the presence of homogeneous and heterogeneous catalysts. This application is incorporated fully into the present invention.

The process according to the invention is preferably performed in a distillation column at least comprising a bottom zone, a reaction zone and a top zone. The bottom zone, reaction zone and top zone are preferably arranged in the sequence stated from the bottom upward in the distillation column. It is not ruled out that reaction also takes place in the bottom or top zone.

In addition, the distillation column may comprise internals with distillative separating action. These additional internals are preferably arranged below and/or above the reaction zone. In the lower separation zone, i.e. the separation zone below the reaction zone, the high-boiling isomerization product is substantially removed from low-boiling components. For example, trans-2-pentenenitrile and trans-3-pentenenitrile are separated from unconverted cis-2-pentenenitrile. In the upper separation zone, i.e. the separation zone above the reaction zone, low-boiling secondary components are substantially removed from high-boiling components. For example, any trans-2-methyl-2-butenenitrile introduced with the reactant stream is separated here from trans-3-pentenenitrile and trans-2-pentenenitrile. It is equally possible to deplete trans-3-pentenenitrile and trans-2-pentenenitrile from unisomerized cis-2-pentenenitrile. These separations are listed merely by way of example and are not restrictive.

In the case of an optimal column configuration, all of the cis-2-pentenenitrile in the reactant stream can thus be converted without an additional reactor, and all of the trans-3-pentenenitrile can be obtained in the bottoms without an additional separating apparatus. The additional internals with distillative separating action (separation zones) are generally advantageous, but not absolutely necessary. For instance, one of the two or both separation zones may also be dispensed with.

The reaction zone consists generally of a plurality of different component regions with different functions. The component regions differ by the task of transporting gas to the top of the column and the task of directing liquid in the direction of the column bottom. In addition, liquid distributors may be needed within the reaction zone in order to ensure optimal distribution of liquid over the column cross section. Internals for introducing heat into the column may also be present in the reaction zone.

EXAMPLES

Example 1

Isomerization of Cis-2-pentenenitrile with Triethylamine as Catalyst

The $C_5$-mononitrile mixture used as the feedstock was prepared according to WO-A-05/73172, example 1, by hydrocyanating 3-pentenenitrile in the presence of Ni(0) complexes which had been synthesized proceeding from a ligand mixture of 60 mol % of tri(m/p-tolyl) phosphite and 40 mol % of the chelate phosphonite 1, and zinc chloride. After removal of adiponitrile, further dinitriles and the Ni(0) catalyst, a $C_5$-nitrile mixture was obtained, which comprised, in addition to trans-3-pentenenitrile (trans-3PN), cis-3-pentenenitrile (cis-3PN) and 4-pentenenitrile (4PN), also cis-2-methyl-2-butenenitrile (cis-2M2BN) (5%), trans-2-methyl-2-butenenitrile (trans-2M2BN) (2%), cis-2-pentenenitrile (cis-2PN) (5%) and trans-2-pentenenitrile (trans-2PN). The percentages are based on the sum of all unsaturated nitriles mentioned.

The $C_5$ mixture was fed to a column K1 which had 30 theoretical plates and was operated at a bottom temperature of 79° C. and a pressure of 100 mbar. cis-2-Pentenenitrile, cis- and trans-2-methyl-2-butenenitrile and triethylamine recycled from column 3 distilled over. The bottom products drawn off were 3-pentenenitrile and trans-2-pentenenitrile, which were recycled into step a), the hydrocyanation of 3-pentene-nitrile.

The top product of column K1, which comprised 79% by weight of cis-2-pentenenitrile and 10% by weight of 2-methyl-2-butenenitriles, was fed to column 2, which possessed 33 theoretical plates and was operated at a bottom temperature of 72° C. and a pressure of 100 mbar.

The top product of column K2 comprised 86% by weight of cis-2-pentenenitrile and 3% by weight of trans-2-methyl-2-butenenitrile. The bottom product discharged from column K2 was a stream which comprised 61% by weight of trans-2-methyl-2-butenenitrile.

The top product from column K2 was fed to a reactor system RS-1 which consisted of a cascade of three stirred tanks. In RS-1, the predominant portion of the cis-2-pentenenitrile isomerization took place at a residence time of 2 hours. Triethylamine losses, for example as a result of discharge, were compensated for by means of a triethylamine feed. The isomerization temperature was 125° C., the pressure 2 bar. The molar ratio of cis-2-pentenenitrile to triethylamine was 1:0.5; the cis-2-pentenenitrile conversion is 13%.

The reaction discharge from reactor system RS-1 was fed to a column K3 which had 15 theoretical plates and was operated at a bottom temperature of 110° C. and a pressure of 250 mbar.

The top product from column K3, which consisted to an extent of 95% by weight of triethylamine, was recycled into the reactor system. A substream which made up 6% by weight of the top product was discharged. A side draw product which consisted to an extent of 79% by weight of cis-2-pentenenitrile was recycled to column K2. High boilers were discharged via the bottom.

The invention claimed is:

1. A process for isomerizing cis-2-pentenenitrile to 3-pentenenitriles, which comprises isomerizing cis-2-pentenenitrile with amidines, tertiary amines or mixtures thereof as a catalyst at a temperature of 80 to 200° C. and a pressure of 0.01 to 50 bar.

2. The process according to claim 1, wherein the catalyst used is a tertiary alkylamine, cycloalkylamine, alkylcycloalkylamine, aminopyridine, imidazole, bicyclic amidine IV or mixtures thereof.

3. The process according to claim 1, wherein the catalyst used is triethylamine.

4. The process according to claim 1, wherein the catalyst used has a boiling point equal to or lower than that of cis-2-pentenenitrile, and higher than that of cis-3-pentenenitrile.

5. The process according to claim 1, wherein the catalyst used has a boiling point 0 to 50° C. lower than that of cis-2-pentenenitrile, and 1 to 50° C. higher than that of cis-3-pentenenitrile.

6. The process according to claim 1, wherein the isomerization of cis-2-pentenenitrile to 3-pentenenitriles is performed in a reaction column.

* * * * *